United States Patent [19]

Palestrant

[11] Patent Number: 4,733,661

[45] Date of Patent: Mar. 29, 1988

[54] GUIDANCE DEVICE FOR C.T. GUIDED DRAINAGE AND BIOPSY PROCEDURES

[76] Inventor: Aubrey M. Palestrant, 6800 N. 47th St., Paradise Valley, Ariz. 85253

[21] Appl. No.: 42,728

[22] Filed: Apr. 27, 1987

[51] Int. Cl.⁴ .............................................. A61B 17/00
[52] U.S. Cl. ........................ 128/303 B; 128/DIG. 26; 604/116
[58] Field of Search ....... 128/303 B, 303 R, DIG. 26; 604/116

[56] References Cited

U.S. PATENT DOCUMENTS

| | | | |
|---|---|---|---|
| 2,409,432 | 10/1946 | Hubbard | 128/DIG. 26 X |
| 2,451,183 | 10/1948 | Tantimonaco | 604/116 X |
| 4,058,114 | 11/1977 | Soldner | 128/303 B X |
| 4,212,297 | 7/1980 | Trosch et al. | 128/DIG. 26 X |

Primary Examiner—Stephen C. Pellegrino
Attorney, Agent, or Firm—Cahill, Sutton & Thomas

[57] ABSTRACT

A handheld guidance device for use in conjunction with a C.T. scanner allows a user to accurately place a catheter within a patient's body. The guidance device includes a generally planar base including a bubble level to aid in maintaining the base horizontal. A needle support arm is pivotally secured to the base adjacent one end thereof, and a cooperating protractor indicates the relative angular relationship between the needle support arm and the base. Needle guides are provided on the support arm for slidingly supporting the catheter at a desired angle as the catheter is inserted into the patient's body. Graduations are marked on the needle support arm for indicating the depth of insertion. A reference line formed upon the base is adapted to be aligned with a transverse light beam projected by the C.T. scanner.

20 Claims, 12 Drawing Figures

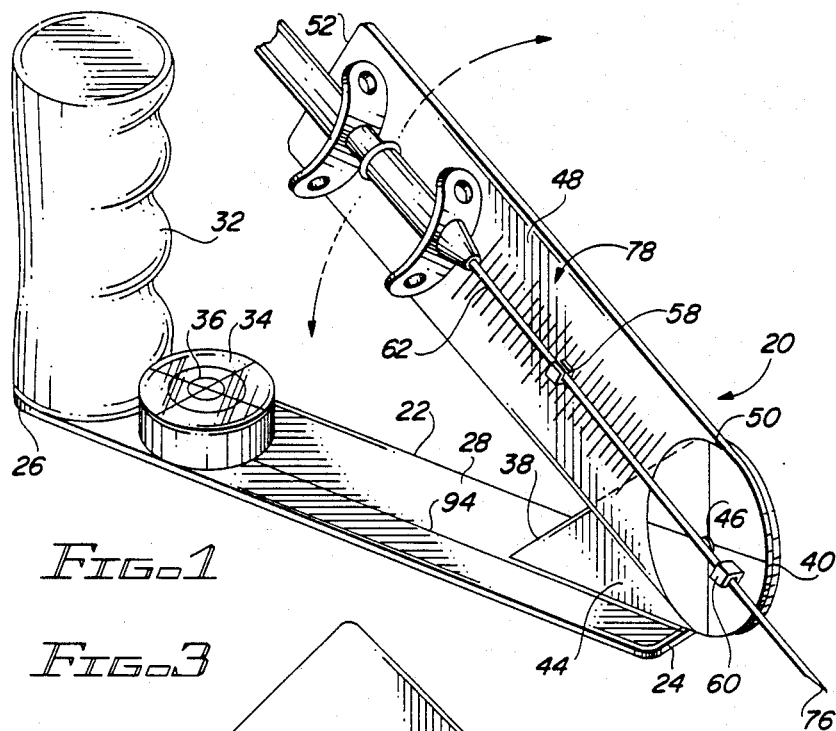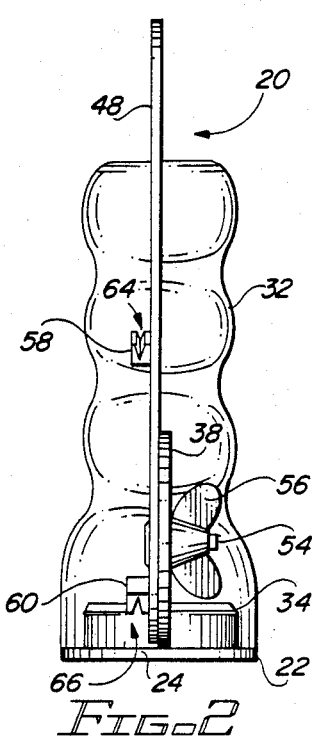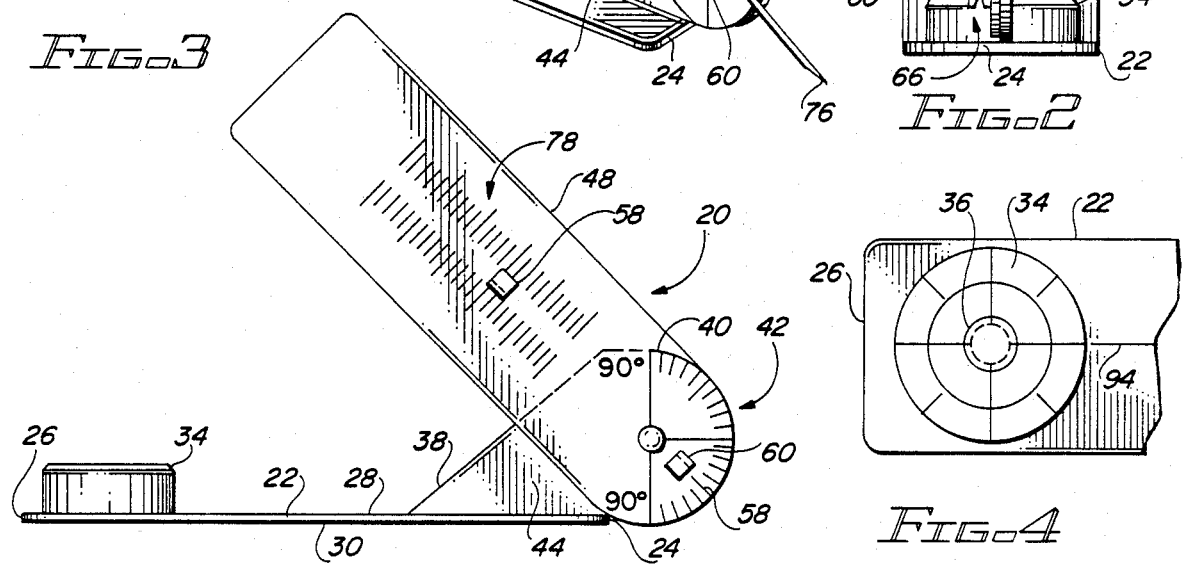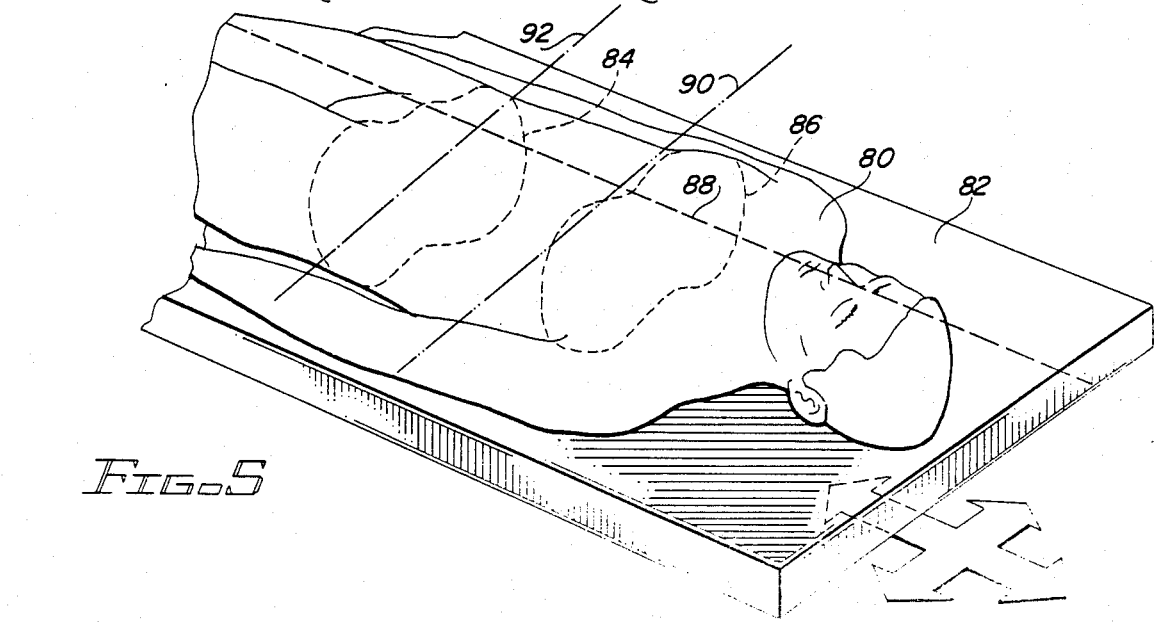

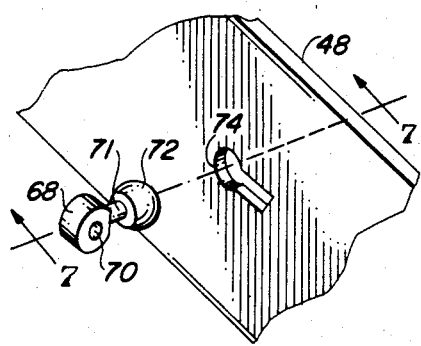
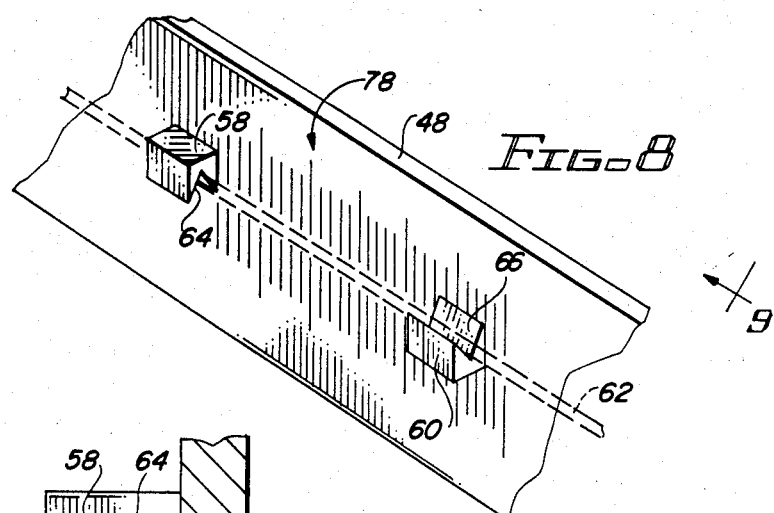
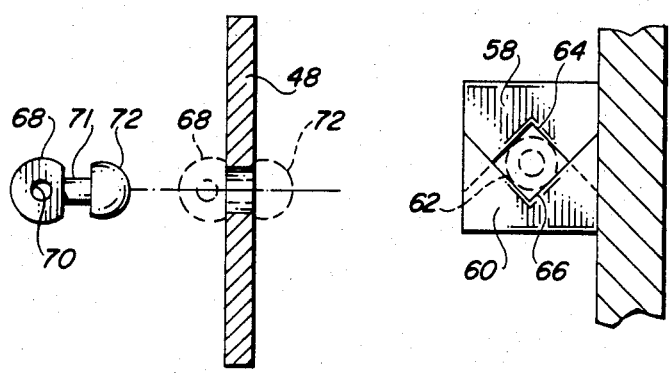
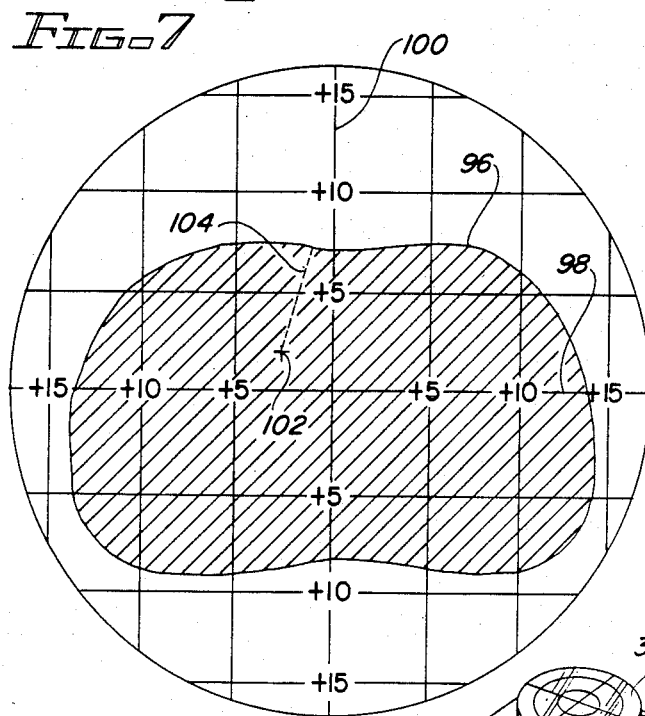
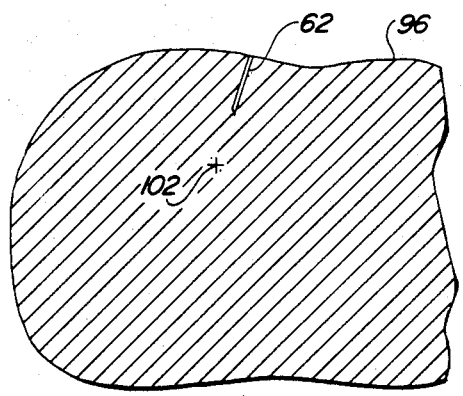
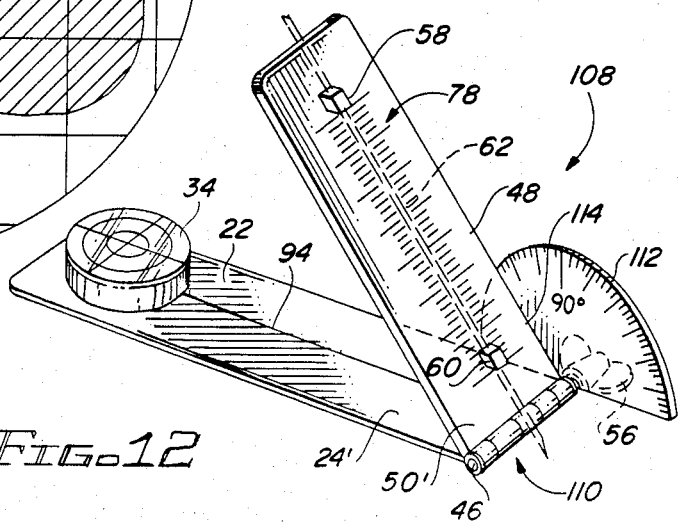

GUIDANCE DEVICE FOR C.T. GUIDED DRAINAGE AND BIOPSY PROCEDURES

BACKGROUND OF THE INVENTION

1. Field of the Invention

The present invention relates generally to apparatus designed to guide a catheter or needle to a preselected point within a patient's body, and more particularly, to a guidance device for inserting biopsy needles, drainage catheters and the like, into a patient's body in conjunction with a C.T. scanner.

2. Description of the Prior Art

In recent years, total body C.T. scanners have become commonly used to provide doctors with a cross-sectional picture of a patient's internal organs and tissues. This imaging modality can define abnormal tissues but, in many situations, cannot determine what has caused the abnormality. Through the use of C.T. scanner technology, physicians are able to accurately place biopsy needles and drainage catheters into abnormal tissues with a high degree of success and with a low morbidity and mortality to the patient. This approach has changed the way in which medical diagnoses are made. For example, exploratory laparotomies for suspected tumors have decreased significantly in recent years in view of the increasing use of C.T. guided biopsies of suspicious masses in the abdomen.

While C.T. scanners that are presently available are capable of measuring a proposed trajectory for a biopsy needle or drainage catheter to within 0.1 millimeters with respect to depth, and within 0.1 degree with respect to angular orientation, there are no known devices available which can accurately and easily utilize such information to properly position a biopsy needle or drainage catheter relative to the patient's body. To the applicant's knowledge, most physicians perform C.T. guided procedures by initially positioning the needle or catheter at a rough estimation of the desired angle, and by then slowly advancing the needle or catheter into the patient's body, taking numerous C.T. scans along the way to determine the actual position of the needle or catheter, and altering its trajectory as needed. This trial and error technique has major disadvantages. First, it usually requires a relatively long period of time and causes the patient to remain in a fixed position which most patients find uncomfortable. Secondly, additional radiation may be harmful to the patient. Additionally, in institutions where C.T. access is limited, a lengthy procedure may excessively utilize the available time, preventing other patients from being studied.

C.T. scanner guided stereotactic brain surgery is known in the art, and various patents disclose frames for attachment to a patient's head for performing a stereotactic surgical procedure. Such stereotactic surgical apparatus for use in conjunction with C.T. scanners is disclosed in U.S. Pat. Nos. 4,341,220 and 4,592,352. The brain, because of its consistent relationship to the boney skull, can have a rigid frame attached to it which can then provide the needed reference coordinates from which various paths can be calculated. However, with respect to other parts of the body, underlying organs and tissues do not bear a constant relationship to the surface anatomy. In addition, parts of the body other than the head lack a sufficiently rigid structure to which a stereotactic frame can be reliably attached.

U.S. Pat. No. 4,058,114 to Soldner discloses a guide aide designed to introduce a puncturing cannula into the body under the guidance of ultrasound imaging equipment. The disclosed apparatus requires that the guide aide be secured to the ultrasound transducer. The disclosed apparatus further requires a targeting aide fastened to the ultrasound image viewing screen. The ultrasound transducer rests upon the patient's body and provides a support for the guide aide. In contrast, C.T. scanners do not utilize a transducer in contact with the pateint's body, and accordingly, the guide aide and targeting aide disclosed by Soldner could not be used in conjunction with C.T. guided interventional procedures.

U.S. Pat. No. 4,583,538 issued to Onik et al. discloses an apparatus designed to facilitate C.T. guided biopsies of the body. The stereotaxis guide instrument disclosed in this patent is floor-mounted and is designed to position a needle guide by moving the same through any of three perpendicular axes. Angular rotations about such axes are permitted to orient the needle guide in any desired direction.

However, the articulated arm configuration disclosed by Onik et al. requires the user to manipulate a great number of cranks, bearings, and arms before a needle can be inserted into the patient.

Accordingly, it is an object of the present invention to provide a guidance device which allows a physician or other user to perform a C.T. guided interventional procedure within a patient's body accurately, easily and more expeditiously than methods or apparatus used in the past to perform such procedures.

It is another object of the present invention to provide such a guidance device which eliminates the need to make repeated C.T. scans in order to insure that the biopsy needle or drainage catheter is correctly aimed toward the target area.

It is still another object of the present invention to provide such a guidance device which quickly and easily converts the angle and depth information provided by the C.T. scanner computer to settings which direct the biopsy needle or drainage catheter to the desired target area.

It is a further object of the present invention to provide a guidance device which is easy to operate and manipulate.

It is a still further object of the present invention to provide such a guidance device which avoids interference with the operation of a biopsy needle or drainage catheter after the same has been inserted into the patient's body.

Yet another object of the present invention is to provide such a guidance device which is of simple and inexpensive construction.

These and other objects of the present invention will become more apparent to those skilled in the art as the description thereof proceeds.

SUMMARY OF THE INVENTION

Briefly described, the present invention is a guidance device allowing a user to accurately place a biopsy needle, drainage catheter, or the like within the body of a patient, and including a base which may be supported in the user's hand, the base preferably being generally planar and extending along a longitudinal axis. A bubble level or similar leveling indicator is secured to the base for indicating whether the longitudinal axis of the base is lying in a horizontal plane. A circular type bubble level provides the advantage of ensuring that both the longitudinal axis of the base and the pivot axis lie in a horizontal plane. A needle support arm is pivotally coupled to the base adjacent an end thereof for movement about a generally horizontal pivot axis. A protractor is provided adjacent the pivotal coupling between the needle support arm and the base for indicating the relative angular relationship therebetween. Needle guides are secured to the needle support arm for slidingly supporting the biopsy needle or drainage catheter at a desired angle, as indicated by the protractor, thereby permitting the user to guide the needle or catheter into the patient's body at the predetermined angle.

In the preferred embodiment of the present invention, a reference line is formed upon the upper surface of the base, the reference line lying within the vertical plane in which the biopsy needle or drainage catheter is supported by the guidance device. The C.T. scanner projects a transverse reference beam of light across the patient's body to indicate the location of the vertical plane through which the scan is being sectioned. In operation, the user positions the base of the guidance device to align the reference line formed thereupon with the aforementioned transverse reference beam of light projected by the C.T. scanner in order to maintain the catheter within the vertical plane of the patient's body being scanned.

The needle support arm has graduated markings formed along its length and allows the user to accurately measure the depth to which the tip of the biopsy needle or drainage catheter has been inserted into the patient's body.

Preferably, the pivotal coupling between the needle support arm and the planar base can be selectively locked at a desired angle in order to maintain the biopsy needle or drainage catheter at such angle during insertion.

Once the biopsy needle or drainage catheter has been placed into the patient's body, the guidance device should be easily removable from the biopsy needle or drainage catheter in order to avoid interference therewith. Accordingly, another aspect of the present invention is the ability of the needle support arm to releasably support the biopsy needle or drainage catheter at the desired angle. In this regard, one embodiment of the present invention utilizes needle guides which are easily disengaged from the biopsy needle or drainage catheter after the same is placed in the body. In an alternate embodiment of the present invention, the needle guides are releasably secured to the needle support arm and are disengaged therefrom after the biopsy needle or drainage catheter is placed in the body.

The guidance device of the present invention preferably includes a handle allowing the user to more easily support the planar base of the guidance device adjacent the patient's body.

BRIEF DESCRIPTION OF THE DRAWINGS

FIG. 1 is a perspective view of a guidance device embodying the present invention.

FIG. 2 is an end view of the guidance device shown in FIG. 1.

FIG. 3 is a side view of the guidance device shown in FIG. 1 wherein a handle has been omitted.

FIG. 4 is a partial top view of the left most portion of the guidance device shown in FIG. 3, including a circular bubble level affixed thereto.

FIG. 5 is a perspective view of a patient lying upon a C.T. scanning table and wherein reference beams of laser light projected by the C.T. scanner are indicated.

FIG. 6 is a partial view of the needle support arm of the guidance device illustrating a needle guide releasably secured thereto.

FIG. 7 is a sectional view of the needle support arm shown in FIG. 6 taken through lines 7—7.

FIG. 8 is a perspective view of a portion of the needle support arm including a pair of offset needle guides directed in opposing directions.

FIG. 9 is an end view of the needle support arm shown in FIG. 8 viewed from lines 9—9.

FIG. 10 is an illustration of a C.T. scanner imaging screen displaying a sectional scan through a patient's abdomen, with superimposed position coordinates.

FIG. 11 is a second C.T. scanner computer screen image showing the tip of the biopsy needle after the same has been inserted into the patient toward the target area.

FIG. 12 is an alternate embodiment of the present invention.

DETAILED DESCRIPTION OF THE PREFERRED EMBODIMENTS

With reference to FIG. 1, a guidance device is identified generally by reference numeral 20 including a generally planar base 22 having a first end 24, an opposing second end 26, and a longitudinal axis extending therebetween. Planar base 22 includes an upper planar surface 28 and an opposing lower surface 30 (see FIG. 3). As shown in FIGS. 1 and 2, a handle 32 may be provided at end 26 of planar base 22, handle 32 being contoured to the user's grip for allowing the user to support guidance device 20 in position relative to a patient's body.

As shown in FIGS. 1-4, a circular bubble level 34 is secured to upper surface 28 of planar base 22 proximate second end 26 thereof. Bubble level 34 includes a bullseye 36 for indicating to a user that planar base 22 is lying in a horizontal plane.

Guidance device 20 also includes a vertical support 38 secured to upper surface 28 of planar base 22 adjacent first end 24 thereof and extending perpendicularly to planar base 22. The right-most (relative to FIG. 3) end 40 of vertical support 38 preferably extends beyond first end 24 of planar base 22 and has a semi-circular contour. Angle markings 42 are formed upon the inner surface 44 of vertical support 38 along the semi-circular periphery of right most end 40 in order to provide a protractor. The radial center of the aforementioned protractor is indicated by reference numeral 46.

As shown in FIGS. 1-3, a needle support arm 48 extends between a first end 50 and a second end 52 and is substantially planar. First end 50 is preferably semi-circularly shaped and has the same radius of curvature as semi-circular end 40 of vertical support 38. Needle support arm 38 is pivotally coupled to end 40 of vertical support 38, the pivotal coupling aligning the radial center of semi-circular end 50 with the radial center 46 of semi-circular end 40. In this manner, needle support arm 48 is maintained perpendicular to planar base 22 and is free to pivot with respect thereto. As shown in FIG. 2, the pivotal coupling between needle support arm 48 and vertical support 38 may be made by a screw 54 passing through aligned holes (not shown) formed in the needle support arm 48 and vertical support 38. Preferably, screw 54 is engaged by a wing nut 56 which, when tightened, locks needle support arm 48 at a predetermined angle relative to planar base 22. Screw 54 passes along the horizontal pivot axis about which needle support arm 48 pivots. This pivot axis lies generally perpendicular to the longitudinal axis of base 22.

In order to permit a user to view the angular markings 42 forming the protractor, semi-circular end 50 of needle support arm 48 is preferably made of a transparent material. A reference line 58 passing through pivotal coupling point 46 and extending along the longitudinal axis of needle support arm 48 is provided for allowing the user to read off from the protractor the present angle of needle support arm 48 relative to planar base 22.

As noted earlier, the guidance device of the present invention is intended to slidingly support a biopsy needle, drainage catheter, or the like upon needle support arm 48. In this regard, a pair of needle guides 58 and 60 are secured to needle support arm 48 for slidingly supporting a biopsy needle, drainage catheter, or the like. Within FIG. 1, a biopsy needle, designated by reference numeral 62, is shown supported by needles guides 58 and 60 for sliding movement along the longitudinal axis of biopsy needle 62. In this manner, a user can slide the shaft of needle 62 along guides 58 and 60 and guide the needle 62 into the patient's body at a desired angle.

As noted above, the guidance device should be easily disengaged from the needle once the needle is properly placed within the patient's body. For example, a physician or other user of the guidance device would probably find it difficult to efficiently operate the biopsy needle in order to obtain a tissue sample if the needle were engaged with the guidance device.

Accordingly, the guidance device shown in FIGS. 1-3 provides needle guide 58 secured to needle support arm 48 at a first point and including a first V-shaped engagement surface 64 forming a channel opening outward in a first direction for slidingly engaging one side of needle 62. Needle guide 60 is secured to needle support arm at a second point spaced apart from needle guide 58 and proximate first end 50 of needle support arm 48. Needle guide 60 also includes a V-shaped engagement surface 66 forming a channel which opens outwardly in a direction opposite to that for engagement surface 64, as shown in FIG. 8. By continuously maintaining the walls of needle 62 engaged with surfaces 64 and 66, as shown in FIG. 9, the user can easily maintain the needle 62 at the desired angle while sliding the same towards its target.

FIGS. 6 and 7 show an alternate form of needle guide which may be used in conjunction with needle support arm 48. As shown in FIG. 6, needle guide 68 includes a hole 70 which is of a size that just permits the shaft of the biopsy needle or drainage catheter 62 to be slidingly passed therethrough. Needle guide 68 includes an enlarged tab 72 connected by a reduced width portion 71. Tab 72 is adapted to be inserted within a slightly oversized hole 74 formed in needle support arm 48. A reduced width channel 75 extends from oversized hole 74 and is adapted to slidingly receive portion 71 of needle guide 68 to releasably lock needle guide 68 to needle support arm 48. Preferably, a pair of such needle guides 68 are releasably secured to needle support arm 48 at spaced apart points lying along the longitudinal axis of the needle support arm 48. The biopsy needle or drainage catheter is caused to pass simultaneously through both of such needle guides to maintain the needle or catheter in proper alignment with needle support arm 48. Once the needle has been placed within the patient, needle guides 68 are slid out of channels 75 and are then released from their cooperating holes 74 in support arm 48, and the remainder of the guidance device is removed, leaving only needle guides 68 in engagement with the shaft of needle 62.

As mentioned earlier, one of the objects of the present invention is to allow a physician or other user to determine the depth of which the tip 76 of biopsy needle 62 has been inserted into the patient's body. For this purpose, periodic graduations, such as centimeter markings, designated generally by reference numeral 78 are printed or otherwise marked upon needle support arm 48. By noting a fixed point upon the needle or catheter, and its relation to the graduations 78, the user can accurately guage the depth to which the tip of the needle or catheter has been inserted.

Referring now to FIG. 5, a patient 80 is shown lying upon a movable, computer-controlled scan table 82 of a C.T. scanning system. Other components of the C.T. scanning system are omitted for clarity. The C.T. scanner is designed to provide a cross-sectional image of the patient's body taken through a vertical scan plane. Two such vertical scan planes are shown in FIG. 5 by dashed lines 84 and 86.

As a reference aide, C.T. scanners are designed to project reference beams of laser light toward the scanning table to indicate the portion of the patient's body being scanned. A first reference beam, indicated by dashed line 88, is projected longitudinally along the center of scanning table 82 to indicate the center point of the scanned image. A first transverse beam of laser light, designated by dashed line 90, is projected by the C.T. scanner indicating the location of the vertical plane through which the patient's body is being scanned. A second transverse beam of laser light, indicated by dashed line 92, is projected by the C.T. scanner a known distance apart from the first transverse beam 90. This second transverse beam of laser light is provided principally to aid a technician or physician in properly positioning the patient's body for scanning before the scanning table is actually advanced into the scanner. It is often difficult for a physician to insert a biopsy needle within the patient's body without moving the scanning table out of the scanning apparatus. Accordingly, the scanning table 82 may be withdrawn from the scanning apparatus by the known distance separating transverse beams 90 and 92 in order to cause transverse beam 92 to overlie the area of the patient's body that was scanned just immediately prior to the movement of scanning table 82.

To help insure that the biopsy needle, drainage catheter or like device will hit its intended target, it is desirable for the user to maintain the needle or catheter within the vertical plane viewed by the C.T. scanner. In this regard, a reference line 94 is formed upon upper surface 28 of planar base 22 extending substantially between first end 24 and second end 26 thereof. Reference line 94 is positioned to lie within the vertical plane that contains the biopsy needle 62 supported by needle support arm 48. In other words, reference line 94 coincides with the vertical projection of biopsy needle 62 onto planar base 22. During use, the user positions planar base 22 so as to maintain reference line 94 in alignment with the appropriate transverse laser light beam 90 or 92 (see FIG. 5), while simultaneously maintaining planar base 22 horizontal, thereby insuring that needle 62 lies within the vertical plane of the patient's body being sectioned by the C.T. scanner.

In order to use guidance device 20, a patient is scanned in conventional fashion to determine the location of the abnormal area. An image, like that shown in FIG. 10, is displayed upon the C.T. scanner computer screen showing a cross-section of the patient's body. The outline of the displayed image is designated within FIG. 10 by reference numeral 96. The computer screen can selectively superimpose an x-axis 98 and a y-axis 100 over the displayed image of the patient's body. Referring briefly to FIG. 5, y-axis 100 corresponds to the position of longitudinal reference beam 88. For purposes of explanation, it will be presumed that the marker designated by reference numeral 102 within FIG. 10 designates the tissue mass that is to be biopsied.

While viewing the computer generated image shown in FIG. 10, the physician determines the best straight line path lying within the sectioned plane of the patient's body to reach target 102 without injuring surrounding organs or blood vessels. Again, for the sake of explanation, it will be presumed that the angled path indicated by dashed line 104 represents the best path for inserting a biopsy needle to reach target area 102. By using a cursor on the computer screen, the radiologist can mark both the target area 102 and the site 106 at which the needle will be inserted. The C.T. scanner computer can then easily compute the distance from insertion site 106 to reference axis 100. The C.T. scanner computer can also be used to display the angle that proposed path 104 forms with either x-axis 98 or y-axis 100. In addition, the C.T. scanner computer is also capable of measuring and displaying the length of the path from insertion site 106 to target area 102.

Once the physician has obtained the information set forth above, the radiologist locates the proposed insertion site upon the patient's body by starting at the intersection of longitudinal light beam 88 and the appropriate transverse beam 90 or 92, and measuring off the distance indicated by the computer between longitudinal beam 88 and entry site 106. A radiopaque marker is placed on this point of the patient's body, and a second scan is performed to confirm that the insertion site has been properly marked. The biopsy needle 62 is then inserted into the guidance device, as shown in FIG. 1, and the needle support arm angle relative to planar base 22 is locked at the angle indicated by the C.T. scanner computer. The user then supports guidance device 20 in close proximity to the patient's body, with the tip 76 of biopsy needle 62 directed toward insertion site 106. The user then views the circular bubble level 34 and adjusts the position of guidance device 20 until planar base 22 is essentially horizontal. Simultaneously, the user adjusts guidance device 20 until reference line 94 coincides with transverse reference beam 90 or 92, as appropriate. Tip 76 of biopsy needle 62 is contacted against insertion site 106, and the user then notes the initial position of biopsy needle 62 relative to the graduated markings 78. The user then advances biopsy needle into the patient's body until the needle has been advanced to the depth indicated by the C.T. scanner computer. Depending upon the size of the lesion or target mass, and its distance from the skin, perhaps one intermediate scan may be desired to insure that needle 62 has not been deflected and is within the selected plane and along the proper trajectory. FIG. 11 illustrates such an intermediate scan with biopsy needle 62 advanced midway toward target area 102.

In FIG. 12 an alternate embodiment of the invention is shown wherein components corresponding to those previously described in regard to FIGS. 1-4 are labeled with corresponding reference numerals. The principal difference between the guidance device 108 shown in FIG. 12 and guidance device 20 shown in FIGS. 1-3 is the manner in which needle support arm 48 is secured to planar base 22. As shown in FIG. 12, the lower end 50' is pivotally coupled to end 24' of planar base 22 by a hinged coupling 110, including hinge pin 46 and releasable locking wing nut 56. A protractor 112 extends perpendicularly from planar base 22 proximate end 24' thereof and adjacent side edge 114 of needle support arm 48 in order to indicate the relative angular relationship between needle support arm 48 and planar base 22. Needle guides 58 and 60 are secured to needle support arm 48 for releasably supporting needle 62. Guidance device 108 is otherwise used in the same manner as guidance device 20.

The guidance devices disclosed herein may easily be manufactured from molded plastic components and are easily assembled. The guidance device is relatively compact and may be packaged and stored in sterile form for ready access by physicians or other users. The guidance device may be quickly and easily locked at the desired angle. Since the guidance device disclosed herein is manually supported, the user can quickly position the guidance device for use adjacent the patient's body without the need to adjust a series of cranks, bearings, or arms in order to make the needle insertion.

Those skilled in the art will now appreciate that a guidance device has been described to facilitate C.T. guided biopsy and fluid drainages in an accurate, easy and relatively prompt manner. While the invention has been described with reference to preferred embodiments thereof, the description is for illustrative purposes only and is not to be construed as limiting the scope of the invention. For example, while the guidance device described herein is described for use specifically with C.T. scanners, those skilled in the art will appreciate that it may also be useful for ultrasound and magnetic resonance scanning as well. In addition, while a circular bubble level is preferred, one or more linear levels may also be used to confirm that the longitudinal axis of the base and/or the pivot axis are horizontal. Various modifications and changes may be made by those skilled in the art without departing from the true spirit and scope of the invention as defined by the apended claims, wherein the term catheter is intended to broadly designate biopsy needles, drainage catheters, or any other form of medical needle or tube.

I claim:

1. A hand-held guidance device for allowing a user to accurately place a catheter within the body of patient, the catheter having a tip and a longitudinal axis, said guidance device comprising in combination:
    a. a base adapted to be manually supported by the user, said base having first and second opposing ends and having a longitudinal axis extending therebetween, said base also having an upper surface;
    b. level means secured to said base for indicating to the user whether the longitudinal axis of said base is lying in a horizontal plane;
    c. a needle support arm pivotally coupled to said base adjacent the first end of said base for pivotal movement about a pivot axis;

d. protractor means disposed proximate to the first end of said base for indicating the relative angular relationship between said needle support arm and said base; and e. needle guide means secured to said needle support arm for supporting the catheter at a predetermined desired angle relative to said base, said needle guide means supporting the catheter for sliding movement along the longitudinal axis of the catheter in order to permit the user to guide the catheter into the patient's body at said predetermined desired angle while the user manually supports said base.

2. A guidance device as recited by claim 1 wherein said level means comprises a generally circular bubble level for indicating whether the longitudinal axis of said base and said pivot axis both lie in a horizontal plane.

3. A guidance device as recited by claim 1 wherein said protractor means is secured to the upper surface of said base and extends substantially perpendicular thereto, said needle support arm being pivotally secured to said protractor means.

4. A guidance device as recited by claim 1 wherein said needle support arm has graduated markings formed thereupon for allowing a user to guage the depth to which the tip of the catheter has been inserted into the patient's body.

5. A guidance device as recited by claim 1 including releasable locking means for releasably locking said needle support arm at said predetermined desired angle relative to said base.

6. A guidance device as recited by claim 1 wherein said needle guide means releasably supports the catheter for allowing the catheter to be disengaged from said needle guide means following the insertion of the catheter into the patient's body.

7. A guidance device as recited by claim 6 wherein said needle guide means comprises:

a. a first guide secured to said needle support arm at a first point thereon and having a first engagement surface generally directed in a first direction, said first engagement surface being adapted to slidingly engage a first side of the catheter; and b. a second guide secured to said needle support arm at a second point thereon spaced apart from said first point and having a second engagement surface generally directed in a second direction opposite to said first direction, said second engagement surface being adapted to slidingly engage a second side of the catheter opposite said first side thereof.

8. A guidance device as recited by claim 1 wherein said needle guide means is releasably secured to said needle support arm for being disengaged therefrom following the insertion of the catheter into the patient's body.

9. A guidance device as recited by claim 8 wherein said needle guide means comprises:

a. a first needle guide releasably secured to said needle support arm at a first point thereon, said first needle guide being adapted to slidingly support the catheter; and b. a second needle guide releasably secured to said needle support arm at a second point thereon spaced apart from said first point, said second needle guide being adapted to slidingly support the catheter.

10. A guidance device as recited by claim 1 including a handle secured to said base, said handle being adapted to be grasped by the user's hand for positioning said base at a desired location with respect to the patient's body.

11. A guidance device for use in conjunction with a C.T. scanner for allowing a user to accurately place a catheter within the body of a patient, the catheter having a tip and a longitudinal axis, the C.T. scanner being adapted to project a transverse reference beam of light across the patient's body to indicate the location of the vertical plane through which the patient's body is being scanned, said guidance device comprising in combination:

a. a base having first and second opposing ends and having a longitudinal axis extending therebetween, said base also having an upper surface;

b. level means secured to said base for indicating to the user whether the longitudinal axis of said base is lying in a horizontal plane;

c. a needle support arm pivotally coupled to said base adjacent the first end of said base for pivotal movement about a pivot axis;

d. protractor means disposed proximate to the first end of said base for indicating the relative angular relationship between said needle support arm and said base; and e. needle guide means secured to said needle support arm for supporting the catheter at a predetermined desired angle relative to said base, said needle guide means supporting the catheter for sliding movement along the longitudinal axis of the catheter in order to permit the user to guide the catheter into the patient's body at said predetermined desired angle;

f. said base including a reference line formed upon the upper surface thereof and extending substantially between the first and second opposing ends of said base, said reference line being positioned to lie perpendicular to said pivot axis and within a vertical plane in which the catheter is supported when said pivot axis is horizontal, wherein the user positions said base to align said reference line with the transverse reference beam of light projected by the C.T. scanner in order to maintain the catheter within the vertical plane of the patient's body being scanned.

12. A guidance device as recited by claim 11 wherein said level means comprises a generally circular bubble level for indicating whether the longitudinal axis of said base and said pivot axis both lie in a horizontal plane.

13. A guidance device as recited by claim 11 wherein said protractor means is secured to the upper surface of said base and extends substantially perpendicular thereto, said needle support arm being pivotally secured to said protractor means.

14. A guidance device as recited by claim 11 wherein said needle support arm has graduated markings formed thereupon for allowing a user to gauge the depth to which the tip of the catheter has been inserted into the patient's body.

15. A guidance device as recited by claim 11 including releasable locking means for releasably locking said needle support arm at said predetermined desired angle relative to said base.

16. A guidance device as recited by claim 11 wherein said needle guide means releasably supports the catheter for allowing the catheter to be disengaged from said needle guide means following the insertion of the catheter into the patient's body.

17. A guidance device as recited by claim 16 wherein said needle guide means comprises:
  a. a first guide secured to said needle support arm at a first point thereon and having a first engagement surface generally directed in a first direction, said first engagement surface being adapted to slidingly engage a first side of the catheter; and
  b. a second guide secured to said needle support arm at a second point thereon spaced apart from said first point and having a second engagement surface generally directed in a second direction opposite to said first direction, said second engagement surface being adapted to slidingly engage a second side of the catheter opposite said first side thereof.

18. A guidance device as recited by claim 11 wherein said needle guide means is releasably secured to said needle support arm for being disengaged therefrom following the insertion of the catheter into the patient's body.

19. A guidance device as recited by claim 18 wherein said needle guide means comprises:
  a. a first needle guide releasably secured to said needle support arm at a first point thereon, said first needle guide being adapted to slidingly support the catheter; and
  b. a second needle guide releasably secured to said needle support arm at a second point thereon spaced apart from said first point, said second needle guide being adapted to slidingly support the catheter.

20. A guidance device as recited by claim 11 including a handle secured to said base, said handle being adapted to be grasped by the user's hand for positioning said base at a desired location with respect to the patient's body.

* * * * *